United States Patent

Neifeld

(10) Patent No.: US 9,320,771 B2
(45) Date of Patent: Apr. 26, 2016

(54) TTO-BASED WIDE SPECTRUM THERAPEUTICS, DISINFECTANTS AND ANESTHETICS FOR USE IN AQUACULTURE

(75) Inventor: Dani Neifeld, Mosha Bney-Yehuda (IL)

(73) Assignee: STOCKTON (ISRAEL) LTD., Petach Tikva (IL)

( * ) Notice: Subject to any disclaimer, the term of this patent is extended or adjusted under 35 U.S.C. 154(b) by 0 days.

(21) Appl. No.: 13/209,410

(22) Filed: Aug. 14, 2011

(65) Prior Publication Data

US 2012/0065273 A1 Mar. 15, 2012

Related U.S. Application Data

(63) Continuation of application No. 12/253,432, which is a continuation-in-part of application No. PCT/IL2007/000503, filed on Apr. 22, 2007, now abandoned.

(30) Foreign Application Priority Data

Apr. 20, 2006 (ZA) .................................. 2006/03149
Apr. 19, 2007 (IL) ........................................... 182665

(51) Int. Cl.
 *A61K 36/61* (2006.01)
(52) U.S. Cl.
 CPC ...................................... *A61K 36/61* (2013.01)
(58) Field of Classification Search
 CPC ........................................................ A61K 36/31
 USPC ......................................................... 424/742
 See application file for complete search history.

(56) References Cited

U.S. PATENT DOCUMENTS

| 4,500,510 | A |   | 2/1985 | Goldstein |
| 5,610,189 | A |   | 3/1997 | Whiteley |
| 5,882,647 | A | * | 3/1999 | Yoshpa ........................ 424/769 |
| 5,998,335 | A |   | 12/1999 | Selga et al. |
| 6,197,305 | B1 |  | 3/2001 | Friedman et al. |
| 6,484,989 | B1 |   | 11/2002 | Connery |
| 6,537,591 | B2 |   | 3/2003 | Yoshpa |
| 2002/0015697 | A1 |  | 2/2002 | Beckman et al. |
| 2004/0096410 | A1 |   | 5/2004 | Maley et al. |
| 2005/0084545 | A1 | * | 4/2005 | Pipko et al. .................... 424/727 |

FOREIGN PATENT DOCUMENTS

| WO | 0135713 | A2 | 5/2001 |
| WO | 2004021792 | A1 | 3/2004 |

OTHER PUBLICATIONS

Novotny et al. "Fish: a potential source of bacterial pathogens for human beings", Vet. Med.—Czech, 49, 2004 (9): 343-358.*
Krajaklang et al., Effects of ethephon on fruit yield, colour and pungency of cayenne and paprika peppers, Australian Journal of Experimental Agriculture 39:1, 86-81 (1999).
Steverding et al., Effect of Australian tea tree oil on Gyrodactylus spp. infection of the three-spined stickleback Gasterosteus aculeatus, Dis Aquat Organ. Aug. 9, 2005; 66(1):29-32.
G. N. Frerichs, Efficacy of chemical disinfectants against snakehead rhabdovirus, J. Appl. Ichthyology 1990, 6, 117.

* cited by examiner

*Primary Examiner* — Chris R Tate
*Assistant Examiner* — Deborah Davis
(74) *Attorney, Agent, or Firm* — Browdy and Neimark, PLLC

(57) ABSTRACT

The invention discloses a novel wide spectrum aquaculture pharmaceutical, comprising a therapeutic, disinfective and/or anesthetize effective amount of a preparation comprising TTO in a stable water-in-oil emulsion of alkali or ammonium salts of organic fatty acid; said emulsion is also stable when converted into an oil-in-water emulsion, wherein the preparation is for the treatment of aquatic animals suffering from a disease selected from bacterial, parasitic, viral and mycotic diseases. The invention also discloses a method for treating diseases selected from bacterial, parasitic, viral and mycotic origin, in an aquatic animal suffering therefrom, which method comprises administering a therapeutic active amount of a preparation comprising TTO in a stable water-in-oil emulsion of alkali or ammonium salts of organic fatty acid; said emulsion is also stable when converted into an oil-in-water emulsion to said aquatic animal.

8 Claims, No Drawings"

TTO-BASED WIDE SPECTRUM THERAPEUTICS, DISINFECTANTS AND ANESTHETICS FOR USE IN AQUACULTURE

This is a continuation of U.S. Ser. No. 12/253,432, filed Oct. 17, 2008 as a continuation-in-part of PCT/IL2007/000503, filed Apr. 22, 2007, claiming Paris Convention priority from ZA 2006/03149, filed Apr. 20, 2006 and from IL 182665, filed Apr. 19, 2007. Paris Convention priority and U.S. domestic benefit from all of these predecessor applications is claimed as appropriate.

FIELD OF THE INVENTION

The present invention generally relates to wide spectrum, TTO-based therapeutics, disinfectants & anesthetics for use in aquaculture, and more specifically, to non-toxic environmentally friendly TTO-based therapeutic and disinfective agents for treating aquaculture, especially bacterial, parasitic, viral and mycotic diseases and for use as anesthetics for edible and ornamental aquatic organisms

BACKGROUND OF THE INVENTION

Fish diseases are not only detrimental to the physiological well being of fish, but also can adversely affect the physical appearance of otherwise viable fish. The prevention, control and treatment of diseases of fish and other aquatic organisms is important in all types of media and growth methods and is particularly important for aquacultures that are kept in artificial or confined environments, such as aquaria, ornamental ponds or aquaculture ponds, as well as various types of shipping containers or holding tanks used for ornamental or edible fish and other aquatic animals.

Aquaculture ponds and shipping conditions often introduce the organisms to stressful situations, e.g., crowding, low oxygen, high carbon dioxide, or contaminated water, causing the organisms to become more susceptible to disease pathogens, such as bacteria, fungi, viruses, and parasites. Such growing and shipping conditions may also expose fish to contaminated water, e.g., from natural waste products of fish or from decaying food or dead fish. Contaminated water is also an environment favoring the growth of pathogens that cause fish diseases.

The intensive use of toxic and environmentally non-friendly disinfectants and therapeutic agents in intensive aquaculture farming, both for edible and for ornamental aquaculture organisms, is a growing concern for human health and the environment. A good example is the infection with atypical strains of *Aeromonas salmonicida* which is known by such names as goldfish ulcer disease, carp erythrodermatitis, and ulcer disease of flounder, eel and salmon. The disease is one of the primary diseases in the aquaculture of edible fish like carp, and Salmon, and in the aquaculture of ornamental fish like goldfish and Koi.

The bacterium causes primary skin lesions and in most cases secondary infection by other bacteria, ectoparasites or fungi frequently, in which case the ulcers continue to develops. In many cases when massive secondary infection of the open ulcer takes place the original pathogen, namely the *Aeromonas salmonicida*, is not present any longer in the ulcer due to unfavorable physiological conditions of the tissue itself.

This primary and secondary infection mechanism poses a big difficulty for the growers. Preventive treatments are essential as fish may be carriers of the *Aeromonas salmonicida*, without exhibiting any clinical signs.

Poor body condition, poor water quality, overstocking, stress and other factors may predispose the fish to an outbreak of ulcerative disease. When an outbreak occurs Antibiotic therapy (such as florfenicol, oxytetracycline, potentiated sulphonamides) in medicated food or injections is used. Bath treatment is often ineffective and not economically worthwhile. All treatment options are costly and require high dosages of Antibiotics. Due to the misleading behavior of the pathogen and its ability to develop resistance to antibiotics, antibiotic therapy should be based on culture and sensitivity results.

When secondary infection frequently takes place a cocktail of drugs is required to cover the possible wide range of secondary pathogens.

The economical losses are huge and even if the fish survive the disease, in many cases noticeable scars are left on the fish which may cause them to be unmarketable, especially with ornamental fish. More and over, fish surviving disease outbreaks are recognized as carriers of the disease and may continue to infect the remaining population without themselves showing any outward signs of infection thus if an effective treatment is not applied to the whole flock, repeated outbreaks and cross contamination in the marketing supply chain (mainly ornamentals) may occur.

No single, nor an environmental friendly treatment which is effective for (i) preventive treatment, and (ii) specific treatment against *Aeromonas salmonicida*, and (iii) broad spectrum treatment against all possible secondary organisms which inhabit the open ulcer, bacteria, Fungi and ectoparasites, and (iv) supporting an effective recovery of the open ulcer and minimal or absence of a scar, it available these days in the market.

Another example is the common practice in fresh water fish against *Saprolegnia*. *Saprolegnia* is ubiquitous in freshwater ecosystems and is the main genus of water molds responsible for significant fungal infections of freshwater fish and eggs.

*Saprolegnia* has a large impact on salmonids, especially those in aquaculture. However, it can also infect a number of other teleosts as well. Channel catfish, pike, bass, elver and suckers, roach, orfe, carp, tench, lamprey, sturgeon, barramundi, *tilapia*, and mullet have been infected with *Saprolegnia*. It has also been associated with tropical fish, including the kissing gourami, guppy, swordfish and platyfish.

Fungal infections are difficult to prevent and treat. Therefore, proper use of chemicals may be necessary when a *Saprolegnia* is diagnosed. However, there are few chemicals approved for use in aquaculture in the United States.

Malachite green is considered the most effective chemical for controlling *Saprolegnia*. However, because of concerns about its potential activity as a carcinogen, teratogen, and/or mutagen, malachite green is banned in the United States and some other countries. Formalin is effective in treating *Saprolegnia* and is the only fungicide registered for use in aquaculture in the United States. However, there are concerns about its affect on both the environment and personnel who handle it.

Both agents, although their use is banned or severely restricted, continue to be used in many places by the industry in an uncontrolled manner due to the lack of effective substitutes. The massive alternative use of antibiotics is also a matter of concern to health and environmental authorities.

The use of anesthetics and antibiotics during transportation of organisms in the aquaculture supply chain is another matter of concern. Ornamental fish packaging systems are characterized by very high fish loading densities and high metabolic wastes in the transport water after shipment. The key limiting factor to increasing the fish loading density in a live—fish transport system is the deterioration of the quality of transport water due to accumulation of metabolic wastes. A variety of techniques have been used to manage this issue. They include starving of the fish before packaging, lowering the temperature of transport water, addition of anesthetics, ion exchange resin and drugs in the transport water. Commonly used compounds for anesthesia during transport include Tricaine (or benzocaine), quinaldine, Eugenol, carbon dioxide and clove oil. Many of the common anesthetic agents impose various limitations. For example, no compound belonging to the Tricaine group should be used within 21 days of harvesting fish for food. Although Quinaldine and Quinaldine Sulfate have been used successfully by fisheries workers, a number of severe adverse effects have been reported. The compounds are irritants to gills and to corneal tissue. In addition, the solvents used to dissolve quinaldine have been known to irritate fishery workers where ventilation of the work area is inadequate. Carbon dioxide gas is soluble in water and as such, has weakly acid properties. Typically the gas is bubbled in the water. It is difficult, however, to control the concentration of carbon dioxide by this method.

Bacterial growth is another major source of metabolic wastes. Bacteria not only increase the amount of metabolic waste but also weaken the fish or cause disease. Drugs such Neomycin sulphate, Methylene blue and Acriflavine, and others that are officially forbidden, are added to the transport water to control bacterial growth.

Many millions of ornamental aquaculture creatures are transported by air in long flights. This extremely stressful journey which in many cases causes a loss of up to 25% of the shipment upon arrival and during the first 7 days of recovery, is a source of major economic loss for the industry. As a result many exporters, although are officially not allowed to do so in the export to certain geographical areas like Europe, add antibiotics to the shipment medium.

No single environmentally friendly agent which combines wide spectrum therapeutic/disinfective (bacteria, fungus, parasites and viruses) properties and anesthetic properties is available in the market or has even been reported.

The transportation issue is not only of concern to the ornamental industry. Starting from treatments in the hatchery farms, through transportation of larva or juveniles to the growth locations (which are sometimes far from the hatchery sites), organism are exposed to intensive stress in the growth ponds in the fish farms as well as during final transportation of mature organisms. Thus, the use of antibiotics (and anesthetics during treatment or transportation), is unfortunately very common, even though it is forbidden in many parts of the world.

Aquaculture is the fastest growing food sector; it pertains to the cultivation of the natural produce of water (e.g., fish, shellfish, algae and other aquatic organisms). Subsets of aquaculture include for example Mariculture (aquaculture in the ocean); Algaculture (the production of kelp/seaweed and other algae); fish farming that is related to the raising of fish such as catfish, tilapia and milkfish in freshwater and brackish ponds or salmon or other fish in marine ponds; fresh and salt water shrimps and crab farming; and the growing of cultured pearls. In 2003, the total world production of fisheries product was 132.2 million tons of which aquaculture contributed 41.9 million tons or about 31% of the total world production. The growth rate of worldwide aquaculture has been very rapid, i.e., more than 10% per year for most species, while the contribution to the total from wild fisheries has been essentially flat for the last decade. Hence for example, in the U.S., approximately 90% of all shrimp consumed is farmed and imported.

Shrimp consumed in the United States are supplied from saltwater or fresh water farms. They all use intensive cultivation methods and the shrimp suffer from many diseases and viruses such as "white spot" and the Taurus virus. Confronting shrimp diseases is very difficult, though there are some processes that can be followed for disease prevention. Here too use of the problematic substances formaldehyde (20 ppm) and green malachite (0.01 ppm) is common. There are no effective antiviral agents for treatment for affected shrimp; viral infection can only be prevented following sanitary preventive methodologies.

Some of the natural products for treating aquaculture diseases disclose products which promote the recovery of injured or diseased fish and other aquatic animals, especially healing of damaged fish tissue; and U.S. Pat. No. 4,500,510 to Goldstein discloses a composition comprising an extract of the aloe vera Linne plant that is used to promote healing of damaged, fish tissue. It may be used with one or more agents for replacing the natural mucoprotein secretion which coats the skin and scales of fish. The composition may be added to either fresh water or salt water. Similarly, U.S. Pat. No. 6,537,591 to Yoshpa discloses a therapeutic method for treating diseased (fungal or bacterial diseases) or injured fish or other aquatic animals that includes administering to the fish or other aquatic animal an amount of *Pimenta* extract selected from the group consisting of *Pimenta racemosa* and *Pimenta dioica* sufficient to promote recovery of the diseased or injured fish or other aquatic animal. Yoshpa also discloses a prophylactic method for treating a disease-free fish or other aquatic animal, including adding Pimento extract selected from the group consisting of *Pimenta racemosa* and *Pimenta dioica* to the water containing or to contain the fish or other aquatic animal in an amount effective to promote resistance of the aquatic animal to bacterial and fungal disease.

U.S. Pat. No. 5,882,647 to Yoshpa discloses another method for promoting recovery of fish from bacterial and fungal diseases and from wounds and abrasions in diseased or injured aquatic animals that includes administering to the aquatic animals an amount of cajeput oil ("Vietnamese Cajeput Oil") which promotes their recovery.

Fish disease therapies which promote inhibiting pathogen growth have an important advantage in reducing the use of potent drugs or chemicals with adverse side effects. Furthermore, treatment of individual diseased or injured fish usually entails exposure of healthy fish and all other beneficial organisms in the environment to the treatment composition as well. For this reason, reducing diseased, injured fish, other aquatic animals or plants also present in the water, are particularly preferred.

TTO is an essential oil characterized by a broad-spectrum antiseptic activity and is a very effective biocide against bacteria and fungi and as an insect repellant. TTO is commercially obtained by distillation of leaves of paperbark tree species *Melaleuca alternifolia*. The tree is indigenous to the moist, sub-tropical coast of northeastern New South Wales and southeast Queensland in Australia, and has evolved its own natural defenses against disease and its own natural repellants against insects.

It is known that the major antiseptic active component of the TTO is the Terpinen-4-ol family. Chemical analysis identified terpinen-4-ol (about 42%), α-terpineol (about 3%) and 1,8-cineole (about 2%), respectively, of tea tree oil) as the water soluble components of tea tree oil. The mode of action of TTO on its cellular target is to damage the pathogen's cell wall and membrane and subsequently to denature the cell constituents. The antiseptic actions of TTO are not impaired in the presence of blood, serum, pus, mucous discharge etc.

An acquired immunity of microorganisms to many antibiotics and sulphonamide drugs does not occur with TTO.

Substantial microbiological testing of TTO has established in the literature typical inhibitory concentrations of the oil against a broad spectrum of microorganisms. Nevertheless, its sharp aromatic characteristics prevent its use "as is" in humans and animals and its phytotoxicity prevents its use in field crops. Many formulations have been suggested in the art, a few of which teach its use in emulsions. None of those formulations has demonstrated broad spectrum activity at an effective dosage on a verity of aquaculture pathogens, including bacteria, fungi, internal and external parasites and viruses, combined with applicability to aquaculture organisms. More so no mentioning was identified in the literature of the anesthetic properties of a given formulation using TTO, let along on the possibility to generate, and based on TTO the only active ingredient, a multipurpose product which is applied as therapeutic, disinfectant and/or anesthetic agent, and is highly useful for a long list of procedures in the aquaculture industry.

The fact that all this is generated with a safe and natural substance and formulation which is very friendly to the environment is only adding to the uniqueness of this invention.

While a few effective TTO-containing emulsion biocides have been published in the literature, none of these have demonstrated the properties mentioned nor have been designed to be used for aquaculture applications, organisms and pathogens. Thus for example, U.S. Pat. No. 5,610,189 to Whiteley discloses a disinfecting composition comprising stable aqueous solutions of (a) a blend of biocide active terpenes from TTO; (b) one or more biocide active surfactants; (c) one or more proton donor type biocides; and (d) a salt of mono, di- or trihydroxy aliphatic or aromatic acid. U.S. Pat. No. 6,197,305 to Friedman et al. discloses a composition for oral hygiene for treating a fungal infection, comprising: a mixture of herbal extracts; a mixture of essential oils such as TTO; and a pharmaceutical carrier; wherein said herbal extracts are each present in an amount of from about 1% to about 10% by weight, and each essential oil is present in an amount of from about 0.2% to about 2.0% by weight. Moreover, it has been shown that tea tree oil inhibits certain fungi (See for example Australian Journal of Experimental Agriculture 39:1, 86-81, 1999). The treatment was satisfactory as it killed the fungi to a large extent, mainly fungi that attack humans, while in plants it caused phytotoxicity to attacked plants.

Steverding et al. have studied the effect of Australian TTO (1-30 ppm) in Tween 80 (10%) emulsions on *Gyrodactylus* spp. infection of the three-spined stickleback *Gasterosteus aculeatus* (See Dis Aquat Organ. 2005 Aug. 9; 66(1):29-32). Gyrodactylids are the only parasitic worms that reproduce in situ on their host and lack a specific transmission stage, therefore they bridge the classical divide between microparasites (bacteria, viruses etc) and macroparasites (worms etc). The study has shows that "TTO has little effect on parasite burdens" and that "TTO does not completely remove all *Gyrodactylus* spp. worms within two days"; moreover, a significant contribution to the TTO efficacy was surprisingly attributed to the Tween 80 emulsifier.

Thus, natural nontoxic wide-spectrum treatments, especially those containing effective organic products, such as the tea tree oil applicable as therapeutic, preventive and as anesthetic agents are thus meeting the ever growing industrial need for safe treatment of aquaculture diseases.

SUMMARY OF THE INVENTION

It is thus the core of the invention to provide a stable therapeutic oil-in-water emulsion for both preventing and curing diseases of aquatic creatures, said emulsion comprising an alkali or ammonium fatty acid salt and 0.1 to 800 ppm (effective therapeutic dosage, ETD) of TTO. It is within the core of the invention that the emulsion is a therapeutic agent useful for controlling a broad spectrum of aquatic pathogens in their aquatic environment including bacteria, fungi, internal and external parasites and viruses. It is further within the core of the invention that the emulsion is adapted to treat both internal and topical diseases of said aquatic creatures. It is further within the core of the invention that the emulsion is possibly non-toxic for specific combinations of said aquatic creatures and said range of ETD. It is further within the core of the invention that the emulsion is stable and effective within fresh, brackish, and salty water.

It is within the scope of the invention to provide such a preparation with antiviral properties, especially adapted to cure viral diseases of infected aquaculture creatures.

It is further within the scope of the invention to provide such a preparation with anti-parasitic properties, especially adapted to cure external, internal, and/or gastrointernal protozoa infections in infected aquaculture creatures.

It is further within the scope of the invention to provide such a preparation such that the effective dosage is non-toxic to algae. The effective dosage in this case is about 0.1 ppm to about 100 ppm.

The preparation possibly is characterized by an aquaculture non-toxic broad spectrum disinfectant or repellant activity selected in a non-limiting manner from fungicidal, bacteriocidal, virucidal, protozoacidal, activities or any mixture thereof. The aquatic animal is selected in a non-limiting manner from fresh water aquatic animals and saltwater aquatic animals. The aquatic animal is further selected in a non-limiting manner from aquatic vertebrates, especially edible and ornamental fish; aquatic invertebrates, especially crabs or shrimps; sponges, especially sea cucumber; snails, clams, oysters and jellyfish.

The present invention also discloses a multi-purpose aquaculture tranquilizer and/or anesthetic pharmaceutical, comprising an effective amount of a preparation comprising TTO in a stable water-in-oil emulsion of alkali or ammonium salts of organic fatty acid; the emulsion is also stable when converted into an oil-in-water emulsion, wherein the said preparation is for the tranquilizing and/or anesthetizing aquatic animals. The aquatic animal is selected in a non-limiting manner from fresh water aquatic animals and salty water aquatic animals. The aquatic animal is further selected in a non-limiting manner from aquatic vertebrates, especially edible and ornamental fish; aquatic invertebrates, especially crabs or shrimps; sponges, especially sea cucumber; snails, clams, oysters and jellyfish.

The present invention also discloses a multipurpose aquatic preparation with therapeutic, tranquilizing, and anesthetic pharmaceutical activity, adapted for treating aquatic creatures, while anesthetizing said aquatic creatures, and said preparation comprising an effective dosage of TTO in a stable oil-in-water emulsion of alkali or ammonium fatty acid salt. It is in the core of the invention that the preparation is useful for administration of an effective dosage while cultivating, prior to or during handling, special procedures (like, just for example, egg harvesting of fertilization treatments), or during transportation of said aquatic creatures.

It is within the scope of the present invention that the multipurpose aquatic preparation is especially adapted to cure viral diseases of infected aquaculture creatures.

It is within the scope of the present invention that the multipurpose aquatic preparation is especially adapted to cure external, internal, and/or gastro-intestinal protozoa infections of aquaculture creatures.

It is within the scope of the present invention that the multipurpose aquatic preparation is non-toxic to algae.

The aquatic animal for which the multipurpose aquatic preparation is adapted is selected from a group of aquatic vertebrates, especially edible and ornamental fish; aquatic invertebrates, especially crabs or shrimps; sponges, especially sea cucumber; snails, clams, oysters and jellyfish.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide aquaculture-oriented non-toxic biocide and/or anesthetic compositions containing TTO (hereinafter 'biocide and anesthetic composition'), and more specifically to provide an effective emulsion containing etheric components obtained biocompatible biocide compositions.

This biocide and anesthetic product comprises TTO and a W/O emulsion. The emulsifier is a water solution of a reaction product of a high molecular weight organic fatty acid and an alkali or ammonium compound. It is in the scope of the invention wherein the W/O TTO-emulsion is converted into a stable O/W emulation final product.

The term 'Effective Therapeutic Dosage' (ETD), as used hereinafter, refers to the amount of TTO content in the formulation as delivered for biocidal or anesthetic purposes.

The term 'tea tree' (i.e., TT) is especially referring hereinafter to *Melaleuca alternifolia* known in the common name "tea tree." More generally, the term is referring to any of the laurel tree family, unusual variety indigenous to the east coast of Australia. The term 'tea tree' is more generally referring hereinafter to any tree of the tea tree family and to other Australian trees or plants of other locations provided for useful essential oil as such as those obtained from tree of the family of the *Eucalyptus*, particularly *Eucalyptus citriodora, Eucalyptus globules, Eucalyptus radiata*; and other plants, such as niaouli oils (*Melaleuca viridiflora*)—Australian Niaouli, also known as broad-leaved paperbark; Australian Blue Cypress; *Kunzea ambigua*, also known as "White cloud" or "White kunzea"; *Lavandula angustifblia* (e.g., Bridestowe), known also as Tasmanian Lavender; Western Australian Sandalwood; White (e.g., Jade) Cypress—Essential oil of *Callitris columellaris/glaucophylla; Citrus bergamia; Mentha piperita; Rosmarinus officinalis*; Pine oils; Essential Oil Blends, such a blends of *Melaleuca alternifolia, Melaleuca quinquenervia nerolidol/linalool*, and *Callitris intratropica* etc.

The term 'tea tree oil' (i.e., TTO) is generally referring hereinafter to any water-miscible and/or water-immiscible ingredient or product obtained from *Melaluca Alternafblia*. Particularly, the term TTO relates to mixtures comprises inter alia terpinen-4-ol, terpinenes, cymenes, pinenes, terpineols, cineole, sesquiterpenes, and sequiterpene alcohols. The term TTO is also referring to any naturally obtained or chemically synthesized of purified composition or comprises of terpinen-4-ol oils, 28-48%; γ-terpinene, 10-28%, α-terpinene, 2.7-13%; 1,8,-cineole, 0.1-16.5%, and various terpenes, 1-25% selected yet not limited to α-pinene, limonene, ρ-cymene and terpinolene. This term is also referring to Phlai Oil, e.g., an essential oil obtained from rhizome *Zingiber cassumunae*.

The term 'emulsion' is referring hereinafter to any water in oil (W/O); oil in water (O/W); W/O/W and/or O/W/O phases comprising the TTO inside, outside or at the surface of aggregates, vesicles, micelles, reversed micelles, nano-emulsions, micro-emulsion, liposomes or in any combination thereof.

The term 'emulsifier' is referring hereinafter to any material or molecule provided as a polymer, oligomer or monomer and is nonionic, anionic or cationic detergent and/or surfactant. The emulsifier is preferably comprises of both lypophilic and hydrophilic portions, such as in saturated or non-saturated long chain alkyl comprising at least one polar or charged atom. It is e.g., in the scope of the invention wherein commercially available Tween 20 ™ emulsifies are used.

For purposes of the present invention, the term "an effective amount for the purpose" is defined as the amount of TTO-based composition which when added to the aquatic media or treated aquatic animal and will control the deleterious organisms, yet will not exhibit aquaculture-toxicity to the culture, because of the specific methods and timing of the addition.

The non-toxic biocide and anesthetic compositions according to the present invention are proved to be environmentally friendly: its principal constituent; TTO, does not pollute nor do the added formulation substances. The compositions are extremely effective biocide and characterized by a wide spectrum, no-gap biocide: sanitizing disinfectant effective against bacteria, viruses, fungi and parasites, a simple 'one-stop' approach. It is a simple application, and simple to monitor: product concentrations can be easily and accurately measured and know to be safe: in its diluted state it is not toxic or have any known carcinogenic or mutagenic effects, nor does it cause corrosion damage to the farm equipment This biocide and anesthetic composition consists in a biocide emulsion comprising TTO and a water emulsion in which the emulsifier is provided in a non-limiting manner by a water solution of a reaction product of a high molecular weight organic fatty acid and an alkali or ammonium compound.

Additionally or alternatively, the emulsions are produced by (a) admixing water-immiscible compositions (e.g., etheric oils, organic fatty acids, tall oil etc); and then (b) admixing water-miscible compositions (e.g., alkali or ammonium salts etc), such that a stable W/O is obtained. Those emulsions are stable, e.g., no phase separation or chemical instability was obtained after 2 years storage at ambient temperature. Hence for example, TTO or its constituents are admixed to the water-immiscible compositions in step (a). Alternatively, a pre-defined measure of the total TTO or its constituents is admixed to the water-immiscible compositions in step (a), whilst the remaining portion is admixed with the water-miscible composition at step (b). It is acknowledged in this respect that admixing is provided e.g., by high rate shearing homogenation, shaking, slow and gentle stirring or any combination thereof.

It is another embodiment of the present invention wherein the aforementioned water immiscible compositions is selected inter alia from high molecular weight fatty acids, fatty acids or a mixture of said acids, wherein those acids are saturated, unsaturated or a combination of the two, one or all referred hereto in the short term 'high molecular weight fatty acids'.

It is another embodiment of the present invention wherein the aforementioned high molecular weight fatty acid comprising linear or branched alkyl chains of C>6 to C<22, especially the range of C>12 to C<18.

It is in the scope of the present invention wherein the aforesaid high weight fatty acids are selected in a non-limiting manner from at least one of the following groups:

tall oil fatty acids, naphthenic acids, rosin acid or any combination thereof;

saturated fatty acids selected from the group of lauric acid, myristic acid, palmitic acid, stearic acid, arahinoic acid, behenic acid, lignocerinic acid or any combination thereof;

unsaturated fatty acids selected from the group of decenoic acid, dodecenoic acid, palamitinoleic acid, oleic acid, lonoleic acid, undecelenic acid, sorbic acid, recinoleic acid or any combination of thereof.

According to yet another embodiment of the present invention, those acids are treated with water miscible compositions, selected in a non-limiting manner from alkali hydroxides, carbonates, bicarbonates or any combination thereof to obtain a salt. Additionally or alternatively, the hereto-defined acids are admixed with sodium, potassium or ammonium compounds, e.g., hydroxides, carbonates, bicarbonates or any combination thereof to obtain a salt.

According to yet another embodiment of the present invention, a water-in-oil emulsion is provided, wherein the TTO concentration is about 10% to about 70% (weight percent), based on the total weight of the emulsion, and, when converted into an oil-in-water emulsion the TTO concentration is between about 1 to about 800 ppm (w/w), based on the total weight of the treated volume.

Freshly prepared salts solution in water give good emulsification of TTO in a wide concentration range. However, it is possible to use industrially prepared alkali salts of organic acid in powder or in granulated form to dissolve the salt obtained in hot water and to use the received solutions for the emulsification of the TTO.

In order to understand the invention and to see how it may be implemented in practice, a plurality of preferred embodiments will now be described, by way of non-limiting example only, with reference to the following examples, wherein all percentages are denoted for weight percents:

The effectiveness of the TTO-based comparisons in treatment of parasitic, bacterial, mycotic and viral disease causing agents of edible and ornamental fish, as well as other aquaculture is hereby presented:

EXAMPLE 1

Parasitology, i.e., Treating of External Parasites in *Tilapia*, Common Carp, Koi and Several Tropical Ornamental Species A formulation containing 66% TTO ("Formulation 66") has been proven to be effective against a wide range of external parasites (Flagellates, Trematodes and Ciliates) of *Tilapia* (Hybrid *Tilapia* and Red *Tilapia aurea*) Common Carp, Koi (*Cyprinus carpio*) and Several Tropical Ornamental Species.

Long term bath treatments with Formulation 66 at an Effective Therapeutic Dosage (ETD) of 10 ppm effectively reduced the level of infection of *Trichodina, Glosatella, Dactylogyrus, Gyrodactylus* and *Costia* species when compared with non-treated/Control groups.

Long term bath treatments with Formulation 66 at an ETD of 10 ppm had limited effect on the level *Ichthiopthyrius multifilis* infection when compared with non-treated/Control groups.

EXAMPLE 2

Bacteriology i.e., treating *Aeromonas* spp and *Myxobacteria* in Common Carp and Several Tropical Ornamental Species Bath treatments with Formulation 66 at an ETD of 10 ppm (every 48 Hours) proved to effectively treat clinical symptoms of Ulcerative Disease of Carp (Carp Erythrodermatosis) caused by Atypical *Aeromonas* Species and *Myxobacteria* species infection of Tropical Ornamentals when compared with non-treated/Control groups.

Consecutive Bath treatments with Formulation 66 at an ETD of 10 ppm (every 48 Hours) proved to effectively prevent clinical symptoms of Ulcerative Disease of Carp (Carp Erythrodermatosis) and *Myxobacteria* species infection of Tropical Ornamentals when compared with non-treated/Control groups.

In a standard "culture and Sensitivity" test, Formulation 66 exhibited inhibition and suppression of Bacterial growth caused by *Aeromonas* spp., the causative agent of Ulcerative Disease of Carp (Carp Erythrodermatosis)

EXAMPLE 3

Mycology i.e., Treating *Saprolegnia* spp

In in-vitro tests, Formulation 66 was found to be effective in inhibiting the growth and development of *Saprolegnia* spp., a common external fungus of Fish.

Consecutive Bath treatments with Formulation 66 at an ETD of 15 ppm (every 48 Hours) provided limited inhibition of *Saprolegnia* spp. when compared with non-treated/Control groups.

Consecutive Bath treatments with Formulation 66 at an ETD of 15 ppm (every 48 Hours) was not effective in preventing mortality caused by existing (severe) infection of *Saprolegnia* spp.

EXAMPLE 4

Anesthetize, i.e., Applying Tranquilizers and Anesthetics to *Tilapia*

Formulation 66 was found to be both an effective and safe tranquilizer and anesthetic of *Tilapia* at the ETD equals 35 to 50 ppm range. This dose was evaluated for 10 to 20 Minute range.

EXAMPLE 5

The Effect of TTO-Compositions of the Present Invention on Ornamental Fish Production, Especially on Growth, Performance and Disease Resistance of Juvenile and Market-Size Guppies Grown in Large Scale Commercial Fish Farm The effect of TTO-based compositions of the present invention was evaluated on growth, performance and disease resistance of Guppies grown in large scale commercial fish farms. The experiment focused on performance and disease prevention during production of juvenile and market size guppies.

Juvenile Guppies were continuously treated during their "Juvenile Production", approximately 14 days, prior to their transfer to the grow-out facility, e.g., their ponds. 16 Vats (8 controls and 8 treatments) of juveniles (3000 to 4000 juveniles per vat) were evaluated. The TTO compositions (ETD=5 ppm TTO) were administered every 48 H. The TTO compositions were administered in the afternoon hours, following the last feeding protocol. Following 14 days of treatment, all treated juveniles were transferred to one net for continuous growth. A second group of non-treated juveniles was transferred to a second net for comparison.

TABLE 1

Survival (%) of various species of Guppies in the presence of TTO-based composition B (66% TTO, 23% Tall oil) vs Control

| | | % Survival | | | % Survival |
|---|---|---|---|---|---|
| *Guppies* sp. A, | | | *Guppies* sp. A | | |
| 1 | Treatment | 75 | 1 | Control | 65 |
| 2 | Treatment | 58 | 2 | Control | 51 |
| 3 | Treatment | 54 | 3 | Control | 54 |
| 4 | Treatment | 87 | 4 | Control | 68 |
| TOTAL | | 68 | TOTAL | | 59 |
| *Guppies* sp B. | | | *Guppies* sp. B | | |
| 1 | Treatment | 92 | 1 | Control | 77 |
| 2 | Treatment | 87 | 2 | Control | 75 |
| 3 | Treatment | 89 | 3 | Control | 84 |
| 4 | Treatment | 90 | 4 | Control | 76 |
| TOTAL | | 90 | TOTAL | | 78 |

The above table 1 shows that the two species of juvenile Guppies treated with the TTO compositions of the preset invention had a significantly higher survival rate compared to non-treated Guppies.

EXAMPLE 6

The Effect of TTO-Compositions (Toxicology) on the Morphological Changes or Behavior Abnormalities in Various Fishes Treatment with TTO compositions of the present invention (ETD=10 ppm), was found safe for various edible and ornamental fishes. This dosage did not produce any morphological changes or behavioral abnormalities in the examined fish. The following fishes were tested: Goldfish (*Carassius awaitus*); Koi (*Cyprinus carpio*); Red *Tilapia aurea*; Thick Lipped Gourami (*C. labiosa*); Dwarf Gourami (*Colisa lalia*); Angelfish (*Pterofillum scalare*); Zebra fish (*Brachidanio rerio*); Suckmouth catfish (*Hypostomus plecostornus*); Guppy (*Poecilia reticulata*); Neon tetra (*Paracheirodon axelrodi*); Flame tetra (*Hyphessobrycon flammeus*); and, White cloud Minnow (*Tanichtys albonubes*).

EXAMPLE 7

Acute Toxicity Experiments; i.e., Determining the Safety Index for Some Four Tto Compositions in Hybrid *Tilapia* (*Aurea×Nilotica*) and Common Carp (*Cyprinus Carpio*)

Experiments were conducted in the Aqua-Vet Wet-lab Facility (Israel) on juvenile Hybrid *Tilapia* (*Aurea×Nilotica*) and Common Carp (*Cyprinus carpio*). The average weight of the *Tilapia* (at stocking) was 12 g. The average weight of the Common Carp (in stocking) was 14 g. All fish were medically evaluated prior to their utilization in these trials and confirmed as "healthy" when entering this trial. The experimental system consists of 12 aerated glass aquaria with an effective water volume of 35 liter each and 24 large tanks with an effective water volume of 250 L each. For every repetition, 10 healthy fish were stocked in each aquarium (5 *Tilapia* and 5 Carp). These fish were transferred to the large vats after 4 days of observation for an additional 14 days of evaluation, namely from the $5^{th}$ day to the $18^{th}$ day. Observations were made 5 times per day in order to detect any sign of disease and/or stress response and in order to count dead animals, which were then removed. This evaluation included visual observation for external signs of disease and/or stress, observation of swimming and breathing behavior and an assessment of willingness to accept feed. In the tanks, all remaining fish were further evaluated for clinical symptoms of disease and physiological indicators of abnormality, such as swimming pattern, feeding activity, breathing patterns, signs of distress, etc. Following 18 days of observation, samples of Fish from each experiment were collected for histo-pathological evaluation.

The bioassay includes five different compositions (four with TTO) (3 repetitions) of the present invention: Composition A—25% TTO, 25% pine oil, 27% tall oil; Composition B—66% TTO, 23% tall oil; Composition C—50% TTO, 35% oleic acid; Composition D—25% TTO, 25% pine oil, 27% oleic acid; Composition E—0% TTO (oil, control).

Composition A displays no morbidity or mortality at an ETD of 20 ppm active ingredient (TTO); partial morbidity and mortality at an ETD of 23 ppm active ingredient. All clinical signs of surviving fish were unapparent after 24 hours.

Composition B displays no morbidity or mortality at an ETD of 10 ppm active ingredient; partial morbidity and mortality at an ETD of 20 ppm active ingredient. All clinical signs of surviving fish were unapparent after 24 Hours.

Composition C displays no mortality at the concentration of an ETD of 800 ppm active ingredient; partial mortality at an ETD of 1600 ppm active ingredient; clinical signs of stress response in all concentrations (from an ETD of 30 ppm active ingredient). Clinical signs of surviving fish were unapparent after 24 Hours. The safety zone of Composition C is significantly and surprisingly higher, as compared to all other formulation tested.

Composition D displays no mortality at ETDs of 5, 10 and 15 ppm (active ingredient); and Total mortality at an ETD of 30 ppm active ingredient.

Composition E displays no mortality at ETDs of 10, 20 and 30 ppm (formulation).

TABLE 2

Fish mortality in 96 hr: (Average Results of 3 Repetitions)

| Tank Number | 1 | 2 | 3 | 4 | 5 | 6 | 7 | 8 | 9 | 10 | 11 |
|---|---|---|---|---|---|---|---|---|---|---|---|
| Composition | .C | .C | .C | .D | .D | .D | E | E | .E | Control | control |
| Active (TTO) (ppm) | 60 | 80 | 100 | 5 | 10 | 15 | 0 | 0 | 0 | | |
| Day 1 | | | | | | | | | | | |
| Tilapia | 0 | 0 | 0 | 0 | 0 | 0 | 0 | 0 | 0 | 0 | 0 |
| Carp | 0 | 0 | 0 | 0 | 0 | 0 | 0 | 0 | 0 | 0 | 0 |
| Day 2 | | | | | | | | | | | |
| Tilapia | 0 | 0 | 0 | 0 | 0 | 0 | 0 | 0 | 0 | 0 | 0 |
| Carp | 0 | 0 | 0 | 0 | 0 | 0 | 0 | 0 | 0 | 0 | 0 |

TABLE 2-continued

Fish mortality in 96 hr: (Average Results of 3 Repetitions)

| Tank Number | 1 | 2 | 3 | 4 | 5 | 6 | 7 | 8 | 9 | 10 | 11 |
|---|---|---|---|---|---|---|---|---|---|---|---|
| Day 3 | | | | | | | | | | | |
| Tilapia | 0 | 0 | 0 | 0 | 0 | 0 | 0 | 0 | 0 | 0 | 0 |
| Carp | 0 | 0 | 0 | 0 | 0 | 0 | 0 | 0 | 0 | 0 | 0 |
| Day 4 | | | | | | | | | | | |
| Tilapia | 0 | 0 | 0 | 0 | 0 | 0 | 0 | 0 | 0 | 0 | 0 |
| Carp | 0 | 0 | 0 | 0 | 0 | 0 | 0 | 0 | 0 | 0 | 0 |
| Day 5-18 | NC* | NC | NC | NC | NC | NC | NC | NC | NC | NC | NC |
| Tilapia | | | | | | | | | | | |
| Carp | | | | | | | | | | | |

*NC not changed

TABLE 3

Fish mortality in 96 hr: (Average Results of 3 Repetitions)

| Tank Number | 1 | 2 | 3 | 4 | 5 | 6 | 7 | 8 | 9 |
|---|---|---|---|---|---|---|---|---|---|
| Formulation | A | A | .A | B | B | B | B | control | control |
| Active (TTO) (ppm) | 6.6 | 19.8 | 23.1 | 10 | 20 | 30 | 35 | | |
| Day 1 | | | | | | | | | |
| Tilapia | 0 | 0 | 5 | 0 | 5 | 5 | 5 | 0 | 0 |
| Carp | 0 | 0 | 3 | 0 | 1 | 4 | 5 | 0 | 0 |
| Day 2 | | | | | | | | | |
| Tilapia | 0 | 0 | 0 | 0 | 0 | 0 | 0 | 0 | 0 |
| Carp | 0 | 0 | 0 | 0 | 0 | 0 | 0 | 0 | 0 |
| Day 3 | | | | | | | | | |
| Tilapia | 0 | 0 | 0 | 0 | 0 | 0 | 0 | 0 | 0 |
| Carp | 0 | 0 | 0 | 0 | 0 | 0 | 0 | 0 | 0 |
| Day 4 | | | | | | | | | |
| Tilapia | 0 | 0 | 0 | 0 | 0 | 0 | 0 | 0 | 0 |
| Carp | 0 | 0 | 0 | 0 | 0 | 0 | 0 | 0 | 0 |
| Total Mortality | | | | | | | | | |
| Tilapia | 0 | 0 | 5 | 0 | 5 | 5 | 5 | 0 | 0 |
| Carp | 0 | 0 | 3 | 0 | 1 | 4 | 5 | 0 | 0 |
| Day 5-18 | NC* | NC* | NC* | NC* | NC* | NC* | NC* | NC* | NC* |
| Tilapia & Carp | | | | | | | | | |

EXAMPLE 8

Effect of TTO-Based Compositions on Phytoplankton Populations

Four TTO-based compositions of the present invention, namely Compositions A-D (See Example 7) were evaluated for their effect on phytoplankton populations. These tests were conducted in 12 aquaria (35 L each) filled with green water from an active fish pond. The compositions were administered as an indefinite bath treatment at ETDs ranging from 20 to 30 ppm. Phytoplankton populations were microscopically evaluated and water "color" was recorded prior to administration of treatment. Exact phytoplankton populations and water "color" of the water were visually compared to the control aquaria after 48 h.

According to microscopic and visual observation, the tested formulation administered as indefinite bath treatment at any ETD from 20 to 30 ppm active ingredient does not effect phytoplankton populations.

EXAMPLE 9

Inhibition of Bacterial Cultures of *Aeromonas Salmonicida*, the Causative Agent of "Carp Erythmodermatosis" i.e., Ulcerative Disease of Carps Ulcerative Disease induces heavy economic loss in *Cyprinus carpio* populations. Atypical *Aeromonas salmonicida* has been determined as the causative agent but some strains of *A. hydrophila* can induce an identical condition.

Four TTO-based compositions of the present invention, namely Compositions A-D (See Example 7) were evaluated in their efficacy to inhibit and prevent growth of atypical *Aeromonas salmonicida*, the causative agent of ulcerative disease of carps on T.S.A. culture media. Every culture plate was inoculated with Gram-negative *Aeromonas* Bacteria obtained from ulcerated Goldfish. Plates were sterile cultures incubated for 24 h at a temperature of 24° C. Inhibition of the TTO-based compositions was compared simultaneously with 2 familiar anti-bacterial medications, namely (i) Tetracycline (30 μg per disc); and (ii), Norfloxacin (10 30 μg per disc). Comparison discs were supplemented in the lab with 20 to 30

µg of the TTO-based compositions each: 50% Composition D; 50% Composition C; and 66% Composition B (See Example 7).

TABLE 4

Zones of inhibition (mm) after 24 h

| Plate # | Comp. D | Comp. C | Comp. B | Tetra. | Nx. |
|---|---|---|---|---|---|
| 1 | 20 | | | 18 | 28 |
| 2 | | | 24 | 18 | 20 |
| 3 | | 18 | | 18 | 20 |
| 4 | | 26 | | 22 | 28 |

All compositions exhibited suppression and inhibition of bacterial growth caused by *Aeromonas* spp., the causative agent of Ulcerative disease. Furthermore, when compared to both Tetracycline (i.e., Tetra) and Norfloxacine (i.e., Nx) these products (at an ETD of 20 µg per disc) showed superior results.

EXAMPLE 10

Evaluation of the Efficacy of the Aforesaid Compositions in Treating External Protozoan Parasitic Infections in *Tilapia*, Koi and Common Carp Clinical evaluation was conducted at the wet-lab facility of AquaVet (Israel). Infected *Tilapia* were stocked into 12 separate Vats. (220 l each). All the fish were stocked following exposure to *Trichodina* Spp. Fish were clinically evaluated prior to the beginning of this phase, and presence of *Trichodina* Spp. within this population was confirmed. Six groups of fish (Treatment #1 to 6) received indefinite bath treatments with the recommended dose. Six groups of fish (Control #1 to 6) did not receive any treatment. Routine monitoring included complete medical examination for bacteria and parasites and a complete evaluation of water quality parameters, such as ammonia, nitrite, temperature, pH and oxygen. Four detailed clinical evaluations were conducted within the 30 day period following treatment: $7^{th}$, $14^{th}$, $21^{st}$ and $28^{th}$ days post treatment. In these evaluations the exact frequency of infected fish in every group was determined. At the end of this phase, the overall effect of the aforesaid compositions was evaluated while considering the following parameters: (i) presence of *Trichodina* Spp. among treated and untreated populations; (ii) presence of secondary infection (bacteria/parasites) among treated and untreated populations; and (iii) morbidity and mortality rates. This protocol was repeated numerous times with various fish species and sizes, and with various species of ectoparasites.

TABLE 6

Evaluation of the efficacy of the aforesaid compositions in treating protozoan parasitic infection causes by *Trichodina* Spp., *Costia* Spp. and *Dactylogirus* Spp. in *Tilapia*:

| Tank | Product | Conc. Active Ingr (TTO) ppm | Parasite | Intensity of Infection (Before) | Intensity of Infection (After) |
|---|---|---|---|---|---|
| 1, 2 | Comp. B | 15 | Trichodina | +++ | |
| | | | Costia | +++ | |
| | | | Dactylogirus | +++ | |
| 3, 4 | Comp. D | 20 | Trichodina | +++ | |
| | | | Costia | +++ | |
| | | | Dactylogirus | +++ | + |
| 7, 8 | Comp. C | 100 | Trichodina | +++ | |
| | | | Costia | +++ | |
| | | | Dactylogirus | +++ | |
| 9, 10 | Comp. A | 20 | Trichodina | +++ | |
| | | | Costia | +++ | |
| | | | Dactylogirus | +++ | |
| 11 | Control | 0 | Trichodina | +++ | +++ |
| | | | Costia | +++ | ++ |
| | | | Dactylogirus | +++ | ++ |
| 12 | Control | 0 | Trichodina | +++ | +++ |
| | | | Costia | +++ | ++ |
| | | | Dactylogirus | +++ | ++ |

TABLE 7

Evaluation of the efficacy of the aforesaid compositions in treating protozoan parasitic infection causes by *Trichodina* Spp. and *Dactylogyrus* Spp. in *Tilapia* and Carp

| Composition | Conc. active ingredient, TTO (ppm) | Infestation level before treatment | Infestation level after treatment |
|---|---|---|---|
| D | 10 | D* = +++ | D = +++ |
| D | 15 | D = +++ | D = +++ |
| B | 10 | D = +++ | D = +++ |
| B | 15 | D = +++ | D = +++ |
| A | 20 | D = +++/T* = +++ | D = +/T = 0 |
| A | 20 | D = +++/T = +++ | D = +/T = 0 |
| C | 150 | D = +++/T = +++ | D = +/T = 0 |
| Control | 0 | D = +++/T = +++ | D = +++/T = +++ |
| Control | 0 | D = +++/T = +++ | D = +++/T = +++ |

D is *Dactylogyrus* Spp., and
T is *Trichodina* Spp.;
Infection levels: 0 = no infection; + = very low; ++ = low; +++ = medium; ++++ = high; +++++ = very high.

EXAMPLE 11

Mixed infection of *Trichodina*, *Glosatella* Spp. and *Dactylogyrus* Spp. in *Tilapia*

TABLE 6

Evaluation of the efficacy of the aforesaid compositions in treating protozoan parasitic infection causes by *Trichodina* Spp. and *Costia* Spp. in *Tilapia*:

| Tank | Product | Conc. (Active Ingr.) | Parasite | Intensity of Infection (Before) | Intensity of Infection (After) |
|---|---|---|---|---|---|
| 1, 2 | Comp. B | 15 ppm | Trichodina | +++ | |
| | | | Costia | +++ | |
| | | | Dactylogirus | +++ | |
| 3, 4 | Comp. D | 20 ppm | Trichodina | +++ | |
| | | | Costia | +++ | |
| | | | Dactylogirus | +++ | + |
| 7, 8 | Comp. C | 100 ppm | Trichodina | +++ | |
| | | | Costia | +++ | |
| | | | Dactylogirus | +++ | |
| 9, 10 | Comp. A | 20 ppm | Trichodina | +++ | |
| | | | Costia | +++ | |
| | | | Dactylogirus | +++ | |

TABLE 6-continued

Evaluation of the efficacy of the aforesaid compositions in treating protozoan parasitic infection causes by *Trichodina* Spp. and *Costia* Spp. in *Tilapia*:

| Tank | Product | Conc. (Active Ingr.) | Parasite | Intensity of Infection (Before) | Intensity of Infection (After) |
|---|---|---|---|---|---|
| 11 | Control | 0 | *Trichodina* | +++ | +++ |
|  |  |  | *Costia* | +++ | ++ |
|  |  |  | *Dactylogirus* | +++ | ++ |
| 12 | Control | 0 | *Trichodina* | +++ | +++ |
|  |  |  | *Costia* | +++ | ++ |
|  |  |  | *Dactylogirus* | +++ | ++ |

TABLE 7

Evaluation of the efficacy of the aforesaid compositions in treating protozoan parasitic infection causes by *Trichodina* Spp. and *Dactylogyrus* Spp. in *Tilapia* and Carp

| Product | Conc. active ingredient (ppm) | Infestation level before treatment | Infestation level after treatment |
|---|---|---|---|
| Comp. D | 10 | D* = +++ | D = +++ |
| Comp. D | 15 | D = +++ | D = +++ |
| Comp. B | 10 | D = +++ | D = +++ |
| Comp. B | 15 | D = +++ | D = +++ |
| Comp. A | 20 | D = +++/T* = +++ | D = +/T = 0 |
| Comp. A | 20 | D = +/T = +++ | D = +/T = 0 |
| Comp. C | 150 | D = +++/T = +++ | D = +/T = 0 |
| Control | 0 | D = +++/T = +++ | D = +++/T = +++ |
| Control | 0 | D = +++/T = +++ | D = +++/T = +++ |

D is *Dactylogyrus* Spp., and
T is *Trichodina* Spp.;
Infection levels: 0 = no infection; + = very low; ++ = low; +++ = medium; ++++ = high; +++++ = very high.

TABLE 8

Evaluation *Trichodina* Spp. infection on dorsal fin of Common Carp (*Cyprinus carpio*)

| Product's name | Dosage a.i., ppm | Level of infestation before treatment | Level of infestation after treatment |
|---|---|---|---|
| Comp. A | 20 | *Trichodina*++++ | *Trichodina*++ |
|  |  | *Dactilogyrus*+ | *Dactilogyrus* 0 |
|  |  | *Centrocestum*+ | *Centrocestum*+ |
| Comp. A | 20 | *Trichodina*+++ | *Trichodina*++ |
|  |  | *Dactilogyrus*+ | *Dactilogyrus* 0 |
|  |  | *Centrocestum*+ | *Centrocestum*+ |
| Comp. B | 15 | *Costia*++ | *Costia* 0 |
|  |  | *Trichodina*++++ | *Trichodina* 0 |
|  |  | *Centrocestum*+ | *Centrocestum*+ |
| Comp. D | 20 | *Trichodina*++++ | *Trichodina*+++ |
|  |  | *Dactilogyrus*+ | *Dactilogyrus*+ |
|  |  | *Centrocestum*+ | *Centrocestum*+ |
| Comp. C | 15 | *Trichodina*++++ | *Trichodina*+++ |
|  |  | *Dactilogyrus*+ | *Dactilogyrus* 0 |
|  |  | *Centrocestum*+ | *Centrocestum*+ |
| Comp. D | 25 | *Trichodina*+++ | *Trichodina*++ |
|  |  | *Gyrodactylus*+ | *Dactilogyrus*+ |
| Comp. A | 25 | *Trichodina*+++ | *Trichodina* 0 |
|  |  | *Dactilogyrus*+ | *Dactilogyrus* 0 |
| Comp. C | 25 | *Trichodina*+++ | *Trichodina*++ |
|  |  | *Gyrodactylus*+ | *Gyrodactylus* 0 |

TABLE 9

Evaluation of the efficacy of the aforesaid compositions in treating protozoan parasitic infection causes by Costia, gill flukes (*Dactylogyrus*) and *Trichodina* in various fish spp. (18° C.).

| Tank | Material | Active ingredient | Kind of fish | Infestation Before treatment | Infestation After 3 treatments | Mortality |
|---|---|---|---|---|---|---|
| T1 | Comp. B | 10 ppm | Gold fish | Costia+++ | Costia++ | 0 |
|  |  |  |  | Dactylogyrus+++ | Dactylogyrus+ |  |
| T2 | Comp. B | 10 ppm | Gold fish | Costia+++ | Costia+ | 0 |
|  |  |  |  | Dactylogyrus+++ | Dactylogyrus++ |  |
| T3 | Comp. B | Control | Gold fish | Costia+++ | Costia+++ | 1 |
|  |  |  |  | Dactylogyrus+++ | Dactylogyrus+++ |  |
| T1 | Comp. B | 10 ppm | *Apistogramma ramirezi* | Trichodina++++ | 0 | 1 |
| T2 | Comp. B | 10 ppm | *Apistogramma ramirezi* | Trichodina++++ | 0 | 1 |
| T3 | Comp. B | Control | *Apistogramma ramirezi* | Trichodina++++ | 0 | 1 |
| T3 | Comp. B | Control | *Apistogramma ramirezi* | Trichodina++++ | 0 | 1 |
| T1 | Comp. B | 10 ppm | Koi | Costia++++ | Costia++ | 2 |
|  |  |  |  | Dactylogyrus+++ | Dactylogyrus++ |  |
| T2 | Comp. B | 10 ppm | Koi | Costia++++ | Costia++ | 3 |
|  |  |  |  | Dactylogyrus+++ | Dactylogyrus++ |  |

TABLE 9-continued

Evaluation of the efficacy of the aforesaid compositions in treating protozoan parasitic infection causes by Costia, gill flukes (*Dactylogyrus*) and *Trichodina* in various fish spp. (18° C.).

| Tank | Material | Active ingredient | Kind of fish | Infestation Before treatment | Infestation After 3 treatments | Mortality |
|---|---|---|---|---|---|---|
| T3 | Comp. B | Control | Koi | Costia++++ | Costia++++ | 4 |
| T1 | Comp. B | 10 ppm | Koi | *Dactylogyrus*+++ Costia++++ | *Dactylogyrus*+++ Costia++ | 2 |
| T2 | Comp. B | 10 ppm | Koi | *Dactylogyrus*+++ Costia++++ | *Dactylogyrus*++ Costia++ | 3 |
| T3 | Comp. B | Control | Koi | *Dactylogyrus*+++ Costia++++ | *Dactylogyrus*++ Costia++++ | 4 |
| T1 | Comp. B | 15 ppm | Koi | *Dactylogyrus*+++ Costia++++ | *Dactylogyrus*+++ Costia+ | 1 |
| T2 | Comp. B | 15 ppm | Koi | *Dactylogyrus*+++ Costia++++ | *Dactylogyrus*++ Costia+ | 0 |
| T3 | Comp. B | Control | Koi | *Dactylogyrus*+++ Costia++++ | *Dactylogyrus*++ Costia++++ | 2 |
| T1 | Comp. B | 10 ppm | *Apistogramma ramirezi* | *Trichodina*++++ | 0 | 1 |
| T2 | Comp. B | 10 ppm | *Apistogramma ramirezi* | *Trichodina*++++ | 0 | 1 |
| T3 | Comp. B | Control | *Apistogramma ramirezi* | *Trichodina*++++ | 0 | 1 |
| T1 | Comp. B | 15 ppm | Koi | Costia++++ | Costia+ | 1 |
| T2 | Comp. B | 15 ppm | Koi | *Dactylogyrus*+++ Costia++++ | *Dactylogyrus*++ Costia+ | 0 |
| T3 | Comp. B | Control | Koi | *Dactylogyrus*+++ Costia++++ | *Dactylogyrus*++ Costia++++ | 2 |
| T1 | Comp. B | 10 ppm | *Ancistrus* | *Dactylogyrus*+++ *Trichodina*++++ | *Dactylogyrus*+++ *Trichodina* 0 | 40% |
| T2 | Comp. B | Control | *Ancistrus* | *Trichodina*++++ | *Trichodina*+++ | 0 |

TABLE 10

Evaluation of the efficacy in treating Protozoan parasitic infection caused by *Trichodina* Spp. and *Gyrodactylus* Spp. In *Tilapia* and Carp (18° C.)

| Product name | Dosage Active ingredient (ppm) | Exposure (min.) | Infestation before treatment | Infestation after treatment |
|---|---|---|---|---|
| Comp. C | 300 | 10 | *Centrocestum*++ *Glosatella*+++ *Trichodina*++++ *Gyrodactylus*++ | *Centrocestum*++ *Glosatella*++ *Trichodina*+++ *Gyrodactylus* 0 |
| Comp. B | 300 | 10 | *Centrocestum*++ *Glosatella*+++ *Trichodina*+++ *Gyrodactylus*++ | *Centrocestum*++ *Glosatella*++ *Trichodina*++ *Gyrodactylus*+ |
| Comp. D | 400 | 10 | *Centrocestum*++ *Glosatella*++++ *Trichodina*+++ *Gyrodactylus*++ | *Centrocestum*++ *Glosatella*+ *Trichodina*++ *Gyrodactylus* 0 |
| Comp. A | 400 | 10 | *Centrocestum*++ *Glosatella*+ *Trichodina*+++ *Gyrodactylus*+ | *Centrocestum*+ *Glosatella* 0 *Trichodina*++ *Gyrodactylus* 0 |
| Comp. C | 300 | 10 | *Centrocestum*++ *Glosatella*+++ *Trichodina*++++ *Gyrodactylus*++ | *Centrocestum*++ *Glosatella*++ *Trichodina*+++ *Gyrodactylus* 0 |
| Comp. B | 300 | 10 | *Centrocestum*++ *Glosatella*+++ *Trichodina*+++ *Gyrodactylus*++ | *Centrocestum*++ *Glosatella*++ *Trichodina*++ *Gyrodactylus*+ |
| Comp. D | 400 | 10 | *Centrocestum*++ *Glosatella*++++ *Trichodina*+++ *Gyrodactylus*++ | *Centrocestum*++ *Glosatella*+ *Trichodina*++ *Gyrodactylus* 0 |
| Comp. A | 400 | 10 | *Centrocestum*++ *Glosatella*+ *Trichodina*+++ *Gyrodactylus*+ | *Centrocestum*+ *Glosatella* 0 *Trichodina*++ *Gyrodactylus* 0 |

TTO-based compositions A-D (See Experiment 7) have been proven to be effective against a wide range of external parasites of various species of *Tilapia* (e.g., Hybrid *Tilapia* and Red *Tilapia aurea*) and of Common Carp (*Cyprinus carpio*).

Composition B has been found to be the most effective compounds at an ETD of 10 to 15 ppm. Long term bath treatments with Composition B at an ETD of 10 ppm effectively reduced the level of infection of *Trichodina, Glosatella, Dactylogyrus, Gyrodactylus* and *Costia* species when compared with non-treated/control groups.

Long term bath treatments with Composition B at an ETD of 10 ppm effectively reduced the level of infection of *Ichthiopthyrius multifilis* in Commmon Carp and Koi (*Cyprinus carpio*) when compared with non-treated/control groups. Short term treatment at an ETD of 15 ppm produced a similar effect.

EXAMPLE 12

Evaluation of Severe Saprolegniosis Infection in Hybrid *Tilapia*

The aforesaid TTO-based compositions were evaluated in providing an effective treatment for apparent clinical infection of *Saprolegnia* in *Tilapia*. 60 healthy *Tilapia* were stocked into 6 separate aquaria. All fish were held in warm temperatures (23° C.) and optimal environmental conditions for 15 days. Following 15 days of optimal environmental conditions, all fish in all 6 aquaria were exposed to decreased water temperatures of 11° C. (hypothermia) and presence (by cohabitation) of severe *Saprolegnia* infection. Infection was introduced by addition of 3 to 4 *Tilapia* (From external Earthen ponds) exhibiting characteristic symptoms of *Saprolegnia*. Four groups of fish (Treatments No. 1 to 4) received consecutive bath treatments with Composition B (every 48 Hours) from the beginning of this experiment. Two groups of fish (Controls No. 1 to 2) did not receive any treatment. Water supply for all the vats in this experiment was based on fresh, chemically balanced water. All fish in this experiment were evaluated on a daily basis. Three detailed clinical evaluations were conducted within the 15 day period following cohabitation and exposure, namely 5th, $10^{th}$ and $15^{th}$ day post cohabitation. In these evaluations we determined the level of *Saprolegnia* infection fish within the six groups of fish. At the end of this phase, we were able to evaluate the overall effect of Composition B in regard to the following parameters: (i) presence of *Saprolegnia* spp. among treated and untreated populations; (ii) presence of secondary infection (bacteria/parasites) among treated and untreated populations; and (iii) morbidity and mortality rates.

TABLE 11

Evaluation of severe Saprolegniosis infection in Hybrid *Tilapia*

| Tank # | Product | Conc. of Active ingredient (ppm) | Intensity of Infection (after 15 days) |
|---|---|---|---|
| 1 | Comp. B | 15 | Saprolegnia (++) |
| 2 | Comp. B | 15 | Saprolegnia (+) |
| 3 | Comp. B | 15 | Saprolegnia (++) |
| 4 | Comp. B | 15 | Saprolegnia (++) |

TABLE 11-continued

Evaluation of severe Saprolegniosis infection in Hybrid *Tilapia*

| Tank # | Product | Conc. of Active ingredient (ppm) | Intensity of Infection (after 15 days) |
|---|---|---|---|
| 5 | Control | 0 | Saprolegnia (+++) |
| 6 | Control | 0 | Saprolegnia (+++) |

Table 11 shows that consecutive bath treatments with Composition B at an ETD of 15 ppm (every 48 h) proved to effectively inhibit the development of *Saprolegnia* spp. in *Tilapia* when compared with non-treated/control groups.

EXAMPLE 13

Anesthesia

A wide variety of compounds have been utilized to anesthetize fish in fisheries research, fisheries management, aquaculture and fish health. The most commonly used anesthetic compounds are tricaine or benzocaine, quinaldine, eugenol and carbon dioxide. The anesthetic was initially used in small tanks and vats on small populations of fish but is now commonly used in various species and in very large volumes of water (earthen ponds) in order to tranquilize and/or anesthetize the fish in the net prior to transfer or selection processes.

TABLE 12

The degree of sedation in fish as a function of the concentration of the compound and of duration of exposure
Stages of Anesthesia

| Stage | Descriptor | Behavioral Response of Fish |
|---|---|---|
| 0 | Normal | Reactive to external stimuli; opercular rate and muscle tone normal |
| 1 | Light sedation | Slight loss of reactivity to external stimuli; opercular rate slightly decreased; equilibrium normal |
| 2 | Deep sedation | Total loss of reactivity to all but strong external stimuli; slight decrease in opercular rate; equilibrium normal |
| 3 | Partial loss of equilibrium | Partial loss of muscle tone; swimming erratic; increased opercular rate; reactivity only to strong tactile and vibration stimuli |
| 4 | Total loss of equilibrium | Total loss of muscle tone and equilibrium; slow but regular opercular rate; loss of spinal reflexes |
| 5 | Loss of reflex reactivity | Total loss of reactivity; opercular movements slow and irregular; heart rate very slow; loss of all reflexes |
| 6 | Medullary collapse (stage of asphyxia) | Opercular movements cease; cardiac arrest usually follows quickly |

TTO-based compositions of the present invention, e.g., Compositions B and C were found to be both an effective (stages 1 to 6) and safe tranquilizer and anesthetic of *Tilapia* in the ETD range of 35 to 50 ppm. This dose was evaluated for a period ranging from 10 to 20 minutes.

EXAMPLE 14

Comparison Between Composition B of the Present Invention and Commercially Available MELAFIX™

Melafix™ by Aquarium Pharmaceuticals is a commercially available all-natural fish medications based on Cajeput Oil. The efficacy of said commercially available products designated for bacteria and fungi against several ectoparasites of ornamental fish and *Tilapia* was evaluated relative to the efficacy of treatment with TTO-based compositions of the present invention.

Melafix™ was applied according to the producer instructions, i.e., 5 ml of commercial product per 40 L of tank water such that 1.35 ppm of active ingredient is obtained. Similarly, Composition B (See experiment 7) was applied in a concentration of 10 ppm (i.e., the ETD of TTO was 6.6 ppm). *Tilapia* fingerlings (avg. 6 g) were introduced into four identical aquaria, 40 L each, with active biofilters and heaters (25° C.) provided in order to simulate conditions of a regular home tank.

Fish were infested by *Trichodina* sp. at the mid level (+++) and *Gyrodactylus* sp. from low to mid level. Melafix™ and Composition B were applied once a day during two days sequentially. Fish mortality was not observed.

TABLE 13

Comparison between Composition B of the present invention and commercially available MELAFIX ™ in *Tilapia*

| Day | Tanks | Applied material | Level of infestation |
|---|---|---|---|
| 1 | T1 | Melafix ™ | *Trichodina*+++, *Gyrodactylus*++ |
|   | T2 | Control | *Trichodina*+++, *Gyrodactylus*++ |
|   | T3 | Composition B | *Trichodina*+++, *Gyrodactylus*+++ |
|   | T4 | Control | *Trichodina*+++, *Gyrodactylus*+++ |
| 2 | T1 | Melafix ™ | *Trichodina*++, *Gyrodactylus*+ |
|   | T2 | Control | *Trichodina*++, *Gyrodactylus*+ |
|   | T3 | Composition B | *Trichodina*+, *Gyrodactylus* 0 |
|   | T4 | Control | *Trichodina*++, *Gyrodactyus*++ |
| 3 | T1 | Melafix ™ | *Trichodina*++, *Gyrodactylus*+ |
|   | T2 | Control | *Trichodina*+, *Gyrodactylus*+++ |
|   | T3 | Composition B | *Trichodina* 0, *Gyrodactylus* 0 |
|   | T4 | Control | *Trichodina*++, *Gyrodactyilus*+++ |

Table 13 shows very good efficacy against *Trichodina* sp. and *Gyrodactylus* sp., i.e., Composition B eliminated the parasites completely. Melafix™ did not show any effect on the parasites.

In a parallel experiment, three aquaria were stocked by 15 gold fish (ave. 7 g). Fish were infested by *Gyrodactylus* sp. (++) and *Dactylogyrus* sp. (+). Tank No. 4 was treated with Melafix™: 5 mL/40 L, i.e., 1.35 ppm of active ingredient. Tank No. 5 was treated by Composition B at an ETD of 10 ppm of active ingredient. Tank No. 6 served as a control and was not treated. The treatment has continued for 6 days, both materials have applied 5 times on daily basis, without water change. Results of the experiment are in the Table 14 below.

TABLE 14

Comparison between Composition B of the present invention and commercially available MELAFIX ™ in gold fish

| Day | Tank | Applied material | Level of infestation |
|---|---|---|---|
| 1 | T4 | Melafix ™ | *Gyrodactylus* sp.++ *Dactylogyrus* sp.+ |
|   | T5 | Composition B | *Gyrodactylus* sp.++ *Dactyilogyrus* sp.+ |
|   | T6 | Control | *Gyrodactylus* sp.++ *Dactilogyrus* sp.+ |
| 3 | T4 | Melafix ™ | *Gyrodactyilus* sp.0 *Dactylogyrus* sp.+ |
|   | T5 | Composition B | *Gyrodactylus* sp.0 *Dactylogyrus* sp.+ |
|   | T6 | Control | *Gyrodactylus* sp.++ *Dactylogyrus* sp.+ |
| 6 | T4 | Melafix ™ | *Gyrodactyilus* sp.++ *Dactylogyrus* sp.+ |
|   | T5 | Composition B | *Gyrodactylus* sp.0 *Dactylogyrus* sp.++ |
|   | T6 | Control | *Gyrodactylus* sp.+ *Dactylogyrus* sp.+ |
| 8 | T4 | Melafix ™ | *Gyrodactyilus* sp.++ *Dactylogyrus* sp.+ |
|   | T5 | Composition B | *Gyrodactylus* sp.0 *Dactylogyrus* sp.++ |
|   | T6 | Control | *Gyrodactylus* sp.+ *Dactylogyrus* sp.+ |
| 9 | T4 | Melafix ™ | *Gyrodactyilus* sp.+++ *Dactylogyrus* sp.++ |
|   | T5 | Composition B | *Gyrodactylus* sp.0 *Dactylogyrus* sp.0 |
|   | T6 | Control | *Gyrodactylus* sp.+ *Dactylogyrus* sp.++ |

Table 14 shows that only Composition B demonstrated a positive effect in the treatment of *Dactylogyrus* and *Gyrodactylus*. No parasites were found in the tank treated by Composition B at the end of test.

EXAMPLE 15

Effect of TTO Based Formulation on the Growth of the Green Alga *Haematococcus Pluvialis*

The effect of TTO-based formulations on the growth of the green alga *Haematococcus pluvialis* and against its main fungal parasite *Chytridiomycota* sp. was demonstrated. The alga is commercially used for the production of carotenoids, astaxanthin; $\alpha$- and $\beta$-carotenes and lutein. The fungal parasite appears during the intensive cultivation of the algae in bioreactors and can cause the death of the entire culture. The TTO formulation tested is a formation containing 66% TTO. Testing Susceptibility of the Parasitic Fungi to the Formulation.

5 mm diameter paper disks with 10% formulation in water were prepared. The disks were dried in an oven and placed in Petri dishes inoculated with *Chytidiomaycota* for 4 days at 32° C., which is the optimal growth temp for the pathogen. The fungus was found to be highly sensitive to the formulation with a full growth inhibition (radius 4 cm) in two separate repetitions.

Range Finding, Infected Algae Culture

Algae cultures were fermented for 7 days and then contaminated with the pathogenic fungus. Five different concentrations (0, 100, 250, 500, and 1000 ppm v/v) were tested. The test cultures were incubated, with constant shaking, at 32° C. Level of fungus inhibition and algae sensitivity were inspected following 6 days of incubation.

TABLE 15

Level of fungus inhibition and algae sensitivity

| Concentration (ppm v/v) | Fungi | Algae |
|---|---|---|
| <100 | No effect | NA |
| 250 | 100% inhibition | No negative effect |
| >500 | 100% inhibition | Partial effect on algae chlorophyll |

EXAMPLE 16

The Effect of TTO-Based Formulation on the Growth of the Green Alga *Haematococcus Pluvialis* Summary of Fresh Water Carp Experiment Fresh water young carp fish (4 cm, 3.5 g) were tested for their sensitivity to a 66% TTO formulation according to the present invention (Composition B). Fish were not fed starting 24 hours prior to the experiment and until 96 hours post treatment. Each treatment aquarium contained 10 fish. Temperature, pH, oxygen and nitrite levels were monitored throughout the 96 hours of the experiment. The monitoring parameters were stable throughout the experiment in all tanks. The pH was 7.3, oxygen ranges were between 96.5 and 98.8% of saturation, and temperature ranges were between 23.7 and 24.5° C.

TABLE 16

Mortality of carp at different TTO concentrations (dead/total alive from last check)

| Concentration ppm v/v | 3 h | 6 h | 12 h | 24 h | 48 h | 96 h |
|---|---|---|---|---|---|---|
| 0 (control) | 0/10 | 0/10 | 0/10 | 0/10 | 0/10 | 0/10 |
| 10 | 0/10 | 0/10 | 0/10 | 0/10 | 0/10 | 0/10 |
| 20 | 0/10 | 0/10 | 0/10 | 0/10 | 0/10 | 0/10 |
| 25 | 0/10 | 0/10 | 0/10 | 0/10 | 0/10 | 0/10 |
| 30 | 0/10 | 0/10 | 0/10 | 0/10 | 0/10 | 0/10 |
| 35 | 7/10 | 0/3 | 0/3 | 0/3 | 0/3 | 0/3 |
| 40 | 9/10 | 0/1 | 0/1 | 0/1 | 0/1 | 0/1 |

All fish mortality occurred within the first 3 hours after application of treatment dosage. Treatment at an ETD of 30 ppm and below was proved to be safe for young carp fish.

EXAMPLE 17

Lethal Dose in Juvenile Shrimp (*Litopenaeus Vannamei*)

The lethal dose in juvenile shrimp (1 to 4 g) was studied. General conditions were as follows: temperature, 25° C.; salinity, 3.3%; oxygen, 4 mg/L; tank volume, 1000 L; 100 individuals per tank; test formulation concentration 1500 ppm (v/v, i.e. the ETD of TTO was 1000 ppm). Individuals were inspected for 12 h after application of treatment dosage. The mortality level was in the range of 10%. Surviving shrimp presented irregular swimming patterns. Based on the experimental results, the recommended safe dosage was determined to be 130 ppm (ETD of TTO=86 ppm), less then 10% of tested concentration.

EXAMPLE 18

Water Treatment for Elimination of Protozoa in Shrimp and Sea Cucumber Farm

General conditions were as follows: temperature, 27° C.; salinity, 3.5%; oxygen, 4 mg/L; tank volume, 100 L; test formulation concentration 1000 ppm (v/v, i.e. the ETD of TTO was 660 ppm). Water was inspected 1 h after application of treatment dosage. Total elimination of protozoa was observed.

EXAMPLE 19

Elimination of *Vorticella* (Protozoa) from Shrimp Larvae (*Litopenaeus Vannamei*)

General conditions were as follows: temperature, 30° C.; salinity, 3.5%; oxygen, 6 mg/L; tank volume, 1000 L; 100,000 individuals per tank; test formulation concentration 50 ppm (v/v, i.e. the ETD of TTO was 33 ppm). Larvae were inspected for 5 h after application of the treatment dosage. Total elimination of *Voticella* with no larva mortality was observed.

EXAMPLE 20

Safety Test for Very High Volume Prophylactic Dose in Juvenile Shrimp (*Litopenaeus Vannamei*)

A very high volume pool of juvenile shrimp (1 to 4 g) was studied. General conditions were as follows: temperature, 31.5° C.; salinity, 3.3%; oxygen, 7 mg/L; pH: 7.2; Pool volume, 18,000 L; total of 4 million individuals in the pool; test formulation concentration 1 ppm (v/v, i.e. the ETD of TTO was 0.7 ppm). Individuals were inspected for 12 h after application of treatment dosage. Neither mortality of larva nor any abnormal swimming patterns were detected. No noticeable damage to nitrification bacteria in the pool was observed.

EXAMPLE 21

Removal of Filamentous Protozoa for the Exoskeleton Appendix of Shrimp Post-Larva General conditions were as follows: temperature, 28° C.; salinity, 3.5%; oxygen, 5 mg/L; tank volume, 100 L; 10,000 individuals per tank; test formulation concentration 200 ppm (v/v, i.e. the ETD of TTO was 130 ppm). Larvae were inspected for 24 h after application of the treatment dosage. Post larvae were inspected for 24 h after application of the treatment dosage. Total removal of filamentous protozoa without alteration of the medium was observed. The physical appearance of the post larval shrimp following treatment typically was excellent.

EXAMPLE 22

Effect of Prophylactic Dosage on Micro-Algae

General conditions were as follows: temperature, 26° C.; salinity, 3.5%; oxygen, 4 mg/L; tank volume, 15 L; micro-algae 40 cells/mL; test concentrations 33, 50, 66, 70, 80 and 90 ppm (v/v, corresponding to ETDs of TTO of 22, 33, 44, 46, 53, and 60 ppm). Water micro-algae were inspected for 24 h after application of treatment dosage. No alternation was detected in the medium. Normal cell appearance was found. Algae maintained normal pigmentation.

EXAMPLE 23

Sensitivity Test for Adult Sea Cucumber (*Holoturia Partialis*)

General conditions were as follows: temperature, 27° C.; salinity, 3.5%; oxygen, 4 mg/L; tank volume, 30 L; a single individual per tank; test concentrations 0.4, 0.6, 0.8, 1.2, 1.6 ppm (v/v, corresponding to ETDs of TTO of 0.3, 0.4, 0.6, 0.8, and 1.1 ppm). Individuals were inspected for 48 h after application of the treatment dosage. Normal organism activity and normal gross anatomy were observed at all test dosages.

EXAMPLE 24

Prophylactic Treatment in Sea Cucumber (*Holoturia Partialis*)

General conditions were as follows: temperature, 26° C.; salinity, 3.5%; oxygen, 4 mg/L; tank volume, 20 L; 10 individuals per tank; test concentrations 33, 50, 66, 70 and 80 ppm (v/v, corresponding to ETDs of TTO of 22, 33, 44, 46, and 53 ppm).

Individuals were inspected for 24 h after application of the treatment dosage. No death or side effects in any of the tested concentrations were detected on any of the specimens. Water protozoa concentration was reduced by 80%.

The results of examples 17 through 24, which were performed in saline environments, taken with the results of examples 1 through 16, which were performed in fresh water environments, demonstrate that the formulation is effective in fresh, brackish, or salt water. These results are surprising because prior art teaches that such an emulsion will be unstable in saline water whereas Composition B and its modifications were found to be stable both in fresh water and in salt water. A further surprising result was the discovery that the maximum safe dosage actually rises in salt water relative to fresh water, again in contrast to that which is taught in the prior art. Moreover, and unexpectedly, the formulation is equally efficacious as a broad-spectrum biocide in salt water as it is in fresh water.

EXAMPLE 25

Effect on Fresh Water Red-Clawed Crayfish (*Cherax Quadricarinatus*)

The effect of a 66% TTO formulation was generally tested on Red-clawed Crayfish. In the first test the $LC_{50}$ of the Red-clawed Crayfish was found to be higher then 10 times the recommended treatment dosage.

In a separate experiment the growth rate of Red-clawed Crayfish treated with the TTO formulation was tested in comparison to an untreated tank and to two other disinfecting agents: formaldehyde and sodium bromide (e.g., commercially available Bromex™).

The growth rates of the three treatment groups (compared to the control group as base reference) were: TTO formulation about 0.1% per day; formaldehyde about 0.08% per day; and Bromex about 0.02% per day. One can thus see from the results of the present experiment that the formulation is an effective growth promoter. Furthermore, one can see from the combined results of experiments 7, 8, 9, 15, 17, 20, 22, 23, and 25 that the formulation is non-toxic to beneficial creatures and algae at ETDs at which it is an effective treatment.

EXAMPLE 26

Effect of TTO Containing Formulation in Adult Shrimps Infected by White Spot Virus White spot virus is a major concern to shrimp growers. Composition B was tested on treatment of adult shrimps with confirmed infection of White Spot Virus. ETD was 100 ppm. All treated shrimps demonstrated significant improvement in all clinical symptoms.

EXAMPLE 2

Effect on Internal Protozoa of Juvenile Shrimp

Juvenile Shrimp treated with Composition B in additional tests have shown significant improvement in eating habits and in quality and volume of secretions. Dissections of treated and untreated specimens were performed and samples of the intestinal content were inspected microscopically. Significant reduction of internal protozoa was observed.

The results of examples 10 and 11 taken in conjunction with, inter alia, those of examples 1, 2, 3, and 9, and 2 demonstrate the efficacy of the formulation against both internal and topical (external) infections and diseases.

EXAMPLE 2

Curative Activity of TTO Containing Formulation in *Vibrio* Spp. Infected Adult Shrimps

*Vibrio* bacteria are very common in shrimp farms. Their main effect is to slow shrimp growth by causing the shrimp to start eating less. The level of the disease is revealed through appearance of red coloration of the antennae, legs and body of the shrimp which develops and spreads as the severity of the disease increases. The level of disease is defined by three stages, with 1 being a light red color of the antennae and 3 being reddish color of the entire body.

In the present experiment, infected adult shrimp at each of the three stages of the disease were treated at ETDs ranging from 100 to 300 ppm. The composition was applied daily for 4 consecutive days. Table 17 presents the ETDs applied on each treatment day for each treatment group.

TABLE 17

Tests results of adult shrimps infected by *Vibrio* at 3 disease levels, following 4 days of consecutive treatment.

| Dosage and stage | Day 1 | 2 | 3 | 4 | Results |
|---|---|---|---|---|---|
| 1 | 100 | 100 | 100 | 100 | By the fourth day all symptoms disappeared. Shrimp were very "alive". Shrimp started eating more. Level of secretions increased. Color of sections changed from dark to pale color (healthy) |
| 2 | 100 | 200 | 200 | 200 | All external symptoms disappeared - 90% by the second day, behavior and secretions improved as in stage 1. |
| 3 | 100 | 300 | 300 | 200 | Improvement in all behavioral parameters, but not all external symptoms disappeared |

Thus we see from examples 1-3, and 26-2, in which the formulation is demonstrated to be effective against parasites, bacteria, protozoa, fungi, and viruses, that the formulation shows a broad spectrum of activity. This result is surprising because no broad spectrum biocidal formulation that is also effective against viruses is known in the prior art. For example, malachite green, which does show a broad spectrum of activity against various parasites and bacteria, is not effective against viral diseases of fish (see, for example, G. N. Frerichs, *J. Appl. Ichthyology* 1990, 6, 117).

The invention claimed is:

1. A method for treating a disease of an aquatic animal, comprising:
adding to a body of water containing the aquatic animal a composition comprising effective amounts of tea tree oil (TTO) and at least one alkali or ammonium salt of an organic fatty acid selected from the group consisting of decenoic acid, dodecenoic acid, palamitinoleic acid, oleic acid, linoleic acid, undecelenic acid, sorbic acid, recinoleic acid, tall oil acids, tall oil fatty acid (TOFA), naftenic acids, rosin acids, lauric acid, myristic acid, palmitic acid, stearic acid, arachidic acid, behenic acid, lignoceric acid, and any mixture thereof, wherein the aquatic animal is selected from the group consisting of tilapia, shrimp, sea cucumber and alga, wherein the disease is caused by a pathogen selected from the group consisting of *Trichodina, Dactylogyrus, Gyrodactylus, Chytridiomycota, Protozoa*, White Spot Virus, and *Vibrio*, and wherein the concentration of the TTO in said body of water is between 10 to 30 ppm.

2. The method according to claim 1, wherein said body of water is selected from the group consisting of water in an aquarium, water in a vat, water in a tank, and a pond.

3. The method according to claim 2, wherein the concentration of TTO in said composition prior to said adding said composition to said body of water is from 20 to 66 wt. %.

4. The method according to claim 1, wherein:

when said aquatic animal is Tilapia, the pathogen is selected from the group consisting of *Trichodina, Gyrodactylus* and *Dactylogyrus;* when said aquatic animal is shrimp, the pathogen is selected from the group consisting of *Protozoa, White Spot Virus* and *Vibrio;* when said aquatic animal is sea cucumber, the pathogen is *Protozoa*; and when said aquatic animal is alga, the pathogen is *Chytridiomycota*.

5. A method for inhibiting pathogen growth in an aquatic animal in an enclosed body of water comprising adding into said enclosed body of water a composition comprising effective amounts of tea tree oil (TTO) and at least one alkali or ammonium salt of an organic fatty acid selected from the group consisting of decenoic acid, dodecenoic acid, palamitinoleic acid, oleic acid, linoleic acid, undecelenic acid, sorbic acid, recinoleic acid, tall oil acids, tall oil fatty acid (TOFA), naftenic acids, rosin acids, lauric acid, myristic acid, palmitic acid, stearic acid, arachidic acid, behenic acid, lignoceric acid, and any mixture thereof, wherein the pathogen is selected from the group consisting of *Trichodina, Dactylogyrus, Chytridiomycota, Gyrodactylus, Protozoa*, White Spot Virus, and *Vibrio*, wherein said aquatic animal is selected from the group consisting of Tilapia, Shrimp, sea cucumber and alga, and wherein said addition is conducted such that the concentration of the TTO in said body of water is 10 to 30 ppm.

6. The method according to claim 5, wherein said enclosed body of water is selected from the group consisting of water in an aquarium, water in a vat, water in a tank, and a pond.

7. The method according to claim 6, wherein the concentration of TTO in said composition prior to said adding to said enclosed body of water is from 20 to 66 wt. %.

8. The method according claim 6, wherein:

when said aquatic animal is Tilapia, the pathogen is selected from the group consisting of *Trichodina, Gyrodactylus* and *Dactylogyrus;* when said aquatic animal is shrimp, the pathogen is selected from the group consisting of *Protozoa, White Spot Virus* and *Vibrio;* when said aquatic animal is sea cucumber, the pathogen is *Protozoa*; and when said aquatic animal is alga, the pathogen is *Chytridiomycota*.

* * * * *